US00PP13561P2

(12) United States Plant Patent
Danziger

(10) Patent No.: US PP13,561 P2
(45) Date of Patent: Feb. 18, 2003

(54) GYPSOPHILA PLANT NAMED 'DANGYPCRYS'

(75) Inventor: Gabriel Danziger, Nir-Zvi (IL)

(73) Assignee: Danziger "DAN" Flower Farm, Post Beit Dagan (IL)

( * ) Notice: Subject to any disclaimer, the term of this patent is extended or adjusted under 35 U.S.C. 154(b) by 0 days.

(21) Appl. No.: 09/899,138

(22) Filed: Jul. 6, 2001

(51) Int. Cl.[7] ..... A01H 5/00

(52) U.S. Cl. ..... Plt./354
(58) Field of Search ..... Plt./354

*Primary Examiner*—Kent L. Bell
(74) *Attorney, Agent, or Firm*—Foley & Lardner

(57) ABSTRACT

A new and distinct Gypsophila plant named 'Dangypcrys' characterized by having relatively weak apicial dominance, straight up growth habit of stems; stable stems, fully branched with a narrow, couic shape; an abundance of medium (8 mm in diameter), semi double type, luminous white flowers; fast growing variety, and flowers exposed to low temperatures (below 10° C.) remain white.

2 Drawing Sheets

LATIN NAME OF THE GENUS AND SPECIES OF THE PLANT CLAIMED

*Gypsophila paniculata.*

VARIETY DENOMINATON

Dangypcrys

BACKGROUND OF THE INVENTION

The present invention relates to a new and distinct cultivar of Gypsophila plant, botanically known as *Gypsophila paniculata*, hereinafter referred to by the cultivar name 'Dangypcrys'.

The new cultivar originated from a cross made in a controlled breeding program in Mishmar Hashiva, Israel.

'Dangypcrys' is a naturally occurring whole plant mutation of cultivar 'Dangysha' (unpatented) selected as a single plant growing among plants of 'Dangysha' in a cultivated environment in Mishmar Hashiva, Israel. The male parent is unknown. Asexual reproduction of the new cultivar by removing cuttings from the original plant was first performed in May, 2000, in Mishmar Hashiva, Israel. Asexual production has demonstrated that the combination of characteristics as herein disclosed for the new cultivar are firmly fixed and retained through successive generations of asexual reproduction, and that the plant reproduces true to type.

BRIEF DESCRIPTION OF THE INVENTION

The following traits have been repeatedly observed and are determined to be basic characteristics of 'Dangypcrys' which in combination distinguish this Gypsophila as a new and distinct cultivar:

1. Relatively weak apicial dominance, straight up growth habit of stems;

2. Stable stems, fully branched and have a narrow, conic shape;

3. Abundance of medium (8 mm in diameter), semi double type, luminous white flowers;

4. Fast growing variety.

5. Flowers exposed to low temperatures (below 10° C.) remain white.

'Dangypcrys' has not been observed under all possible environmental conditions. The phenotype of the new cultivar may vary significantly with variations in environment such as temperature, light intensity, and day length without any change in the genotype of the plant. The following observations, measurements and values describe the new cultivar as grown in Mishmar Hashiva, Israel under conditions which closely approximate those generally used in commercial practice.

Of the many commercial cultivars known to the present inventor, the most similar in comparison to 'Dangypcrys' is cultivar 'Bristol Fairy' (unpatented). In comparison to 'Bristol Fairy', 'Dangypcrys' has longer stems, more upright growth habit, narrower inflorescence formation, smaller flowers, and easier handling.

In comparison to the parental cultivar, 'Dangypsha', 'Dangpycrys' flowers one week earlier and its flowers do not turn pink even in temperatures as low as 5° C.

BRIEF DESCRIPTION OF THE DRAWINGS

The accompanying photographic drawings show typical flowers and foliage of 'Dangypcrys', with colors being as true as possible with illustrations of this type.

FIG. 1 is a close-up view of the flower of the new cultivar.

FIG. 2 is a front view of a flowering stem of the new cultivar.

DETAILED BOTANICAL DESCRIPTION

The following observations, measurements and values describe a 3 month old plant of 'Dangypcrys' as grown in Mishmar Hashiva, Israel under conditions which closely approximate those generally used in commerical practice. Color references are made to The Royal Horticultural Society Colour Chart (R.H.S.), except where general colors of ordinary significance are used.

Propagation: Cuttings of side shoots.

Plant:

*General appearance and form.*—Height: 100–120 cm. Width: 50–60 cm.

*Habit.*—Upright bush made of 8–10 flowering stems forming a rosette.

*Flowering response.*—Long day.

*Flowering season.*—All year round when supplemented with lighing; natural flowering when day length extends 12 hours.

*Winter hardiness.*—Tolerant to temperatures as low as 0° C.

*Lastingness of the individual bloom.*—8–10 days both on and off the plant (vase life).

*Rooting.*—Rooting hormone used.

*Fragrance.*—Typical of gypsophila.

Foliage:

*Shape of leaf.*—Lanceolate. Base: Ovate. Tip: Acuminate.

*Margin.*—Entire.

*Texture.*—Smooth.

*Size.*—Length: 12 cm. Width: 20 mm.

*Main color of upper surface.*—Mature leaf: Yellow-Green RHS 147 A. Immature leaf: Yellow-Green RHS 147 A.

*Main color of lower surface.*—Mature leaf: Green RHS 137 A. Immature leaf: Green RHS 137 A.

*Venation color.*—None.

*Attachement.*—Sessile.

*Stipules.*—None.

Inflorescence:

*Natural flowering season.*—During long day conditions.

*Corolla.*—Average Number: Hundreds. Diameter: 8 mm. Petal Size: 3 mm in length, 1 mm in width. Petal Margin: Entire with emarginated tip. Petal Number: Approximately 30. Petal Shape: Spathulated with emarginated tip. Petal Markings: None. Dorsal Petals: Free. Lateral Petals: Free. Petal Color: White RHS 155 D (both upper and lower surfaces). Sepal number: 5. Sepal shape: Lanceolate. Sepal length: 2 mm. Sepal apex: Acute. Sepal margin: Entire. Sepal color: Yellow-green RHS 147 B (both surfaces).

*Stem.*—Average length: 100–120 cm. Average diameter: 5 mm. Color: Yellow-Green RHS 144 B. Internode length: 10–12 cm.

*Spur.*—Color: None.

*Bud.*—Response: Long day conditions. Color: Green RHS 146 B and white RHS 155 D. Size before opening: 2–3 mm in diameter. Pedicel Length: 9–12 mm. Pedicel Color: Yellow-Green RHS 144 B.

Reproductive organs:

*Stamen.*—Deformed.

*Anthers.*—Deformed.

*Stigma.*—2, white RHS 155 D.

*Ovary.*—Green RHS 145 B.

Disease resistance: Not susceptible to most pests and diseases common in commercial fields, under regular growing conditions.

I claim:

1. A new and distinct Gypsophila plant named 'Dangypcrys', substantially as illustrated and described herein.

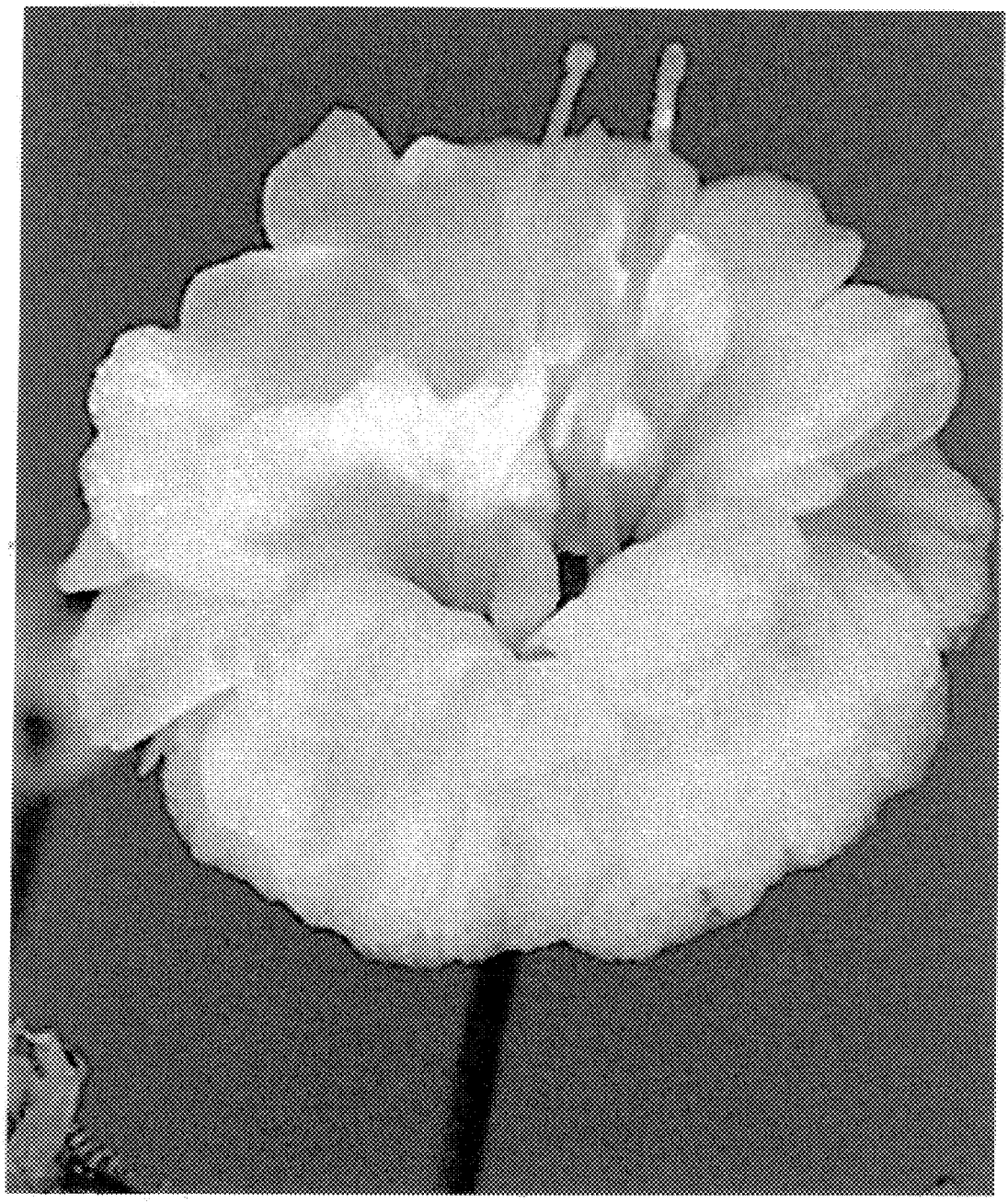

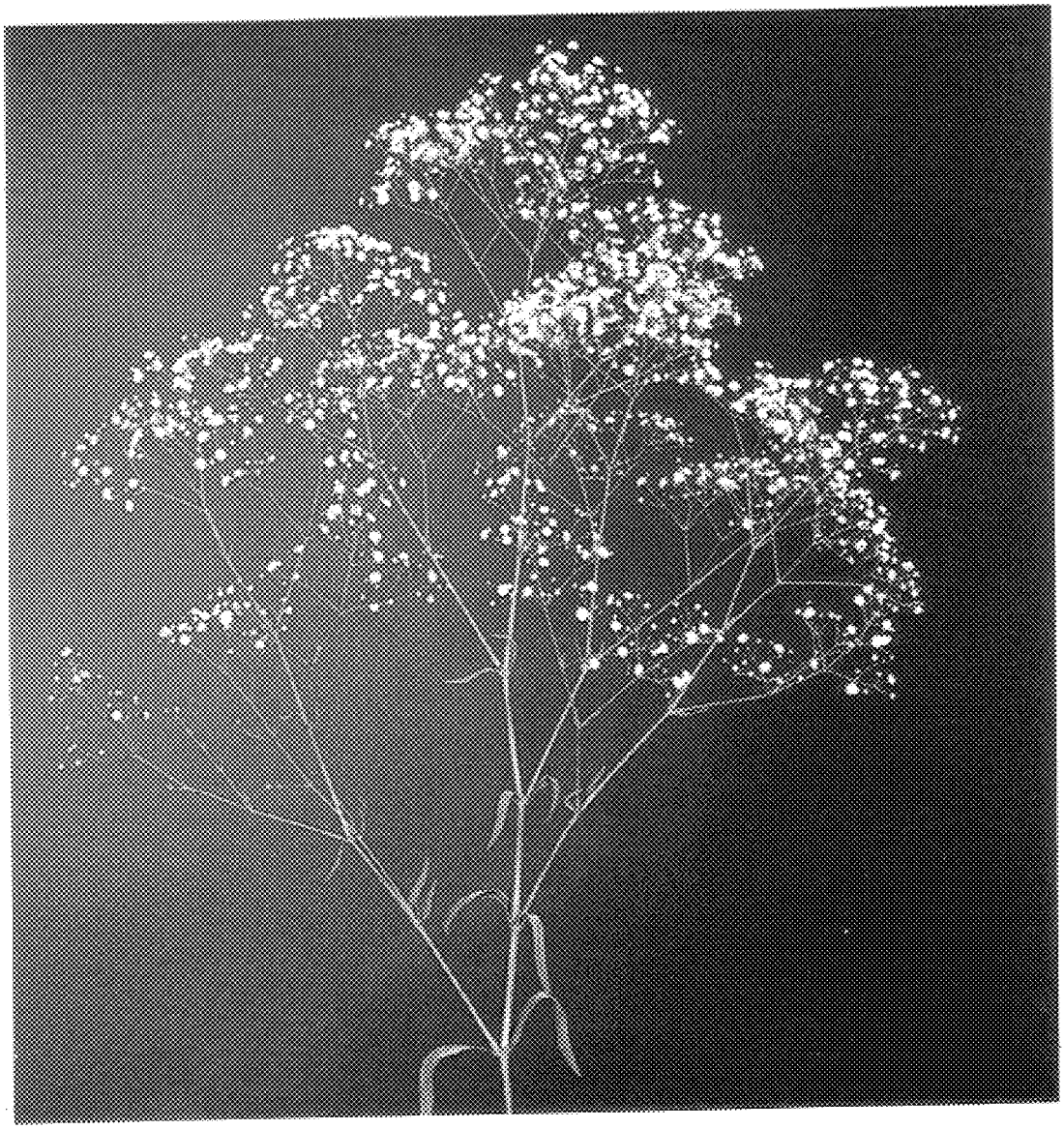

* * * * *